(12) United States Patent
Cabiri et al.

(10) Patent No.: US 10,610,639 B2
(45) Date of Patent: Apr. 7, 2020

(54) NEEDLE INSERTION AND RETRACTION MECHANISM

(71) Applicant: West Pharma. Services IL, Ltd., Ra'anana (IL)

(72) Inventors: Oz Cabiri, Hod Hasharon (IL); Ran Hezkiahu, Herzliya (IL); Tal Hammer, Ramat-Gan (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/340,586

(22) PCT Filed: Oct. 10, 2016

(86) PCT No.: PCT/US2016/056238
§ 371 (c)(1),
(2) Date: Apr. 9, 2019

(87) PCT Pub. No.: WO2018/070978
PCT Pub. Date: Apr. 19, 2018

(65) Prior Publication Data
US 2019/0231973 A1    Aug. 1, 2019

(51) Int. Cl.
*A61M 5/142* (2006.01)
*A61M 5/145* (2006.01)
(Continued)

(52) U.S. Cl.
CPC ...... *A61M 5/14248* (2013.01); *A61M 5/1454* (2013.01); *A61M 5/3287* (2013.01);
(Continued)

(58) Field of Classification Search
CPC ............ A61M 5/3287; A61M 5/14248; A61M 2005/14252; A61M 2005/14256; A61M 2005/1585
See application file for complete search history.

(56) References Cited

U.S. PATENT DOCUMENTS

| 5,858,001 A | 1/1999 | Tsals et al. |
| 6,189,292 B1 | 2/2001 | Odell et al. |

(Continued)

FOREIGN PATENT DOCUMENTS

| JP | 2013519473 | 5/2013 |
| JP | 2016525428 | 8/2016 |

(Continued)

OTHER PUBLICATIONS

Int'l Search Report and Written Opinion dated Jul. 12, 2017 in Int'l Application No. PCT/US2016/056238.

(Continued)

*Primary Examiner* — Laura A Bouchelle
(74) *Attorney, Agent, or Firm* — Panitch Schwarze Belisario & Nadel LLP

(57) ABSTRACT

A needle insertion and retraction mechanism for a drug delivery device, comprises a motion source, a user-operated control for the motion source, an interrupter for stopping motion of the motion source at a predetermined location and thereby dividing the motion into two parts which are continuous relative to each other. A motion translation mechanism connects the source of continuous motion to a needle, to extend the needle during the first motion part and to retract the needle during the second motion part. The needle is thus extended and retracted by continued operation of a single tension source rather than two tension sources operating in opposition to each other. The motion source may be a spring, and a winding mechanism may be provided to wind the spring. The second motion part may be initiated by pulling the adhered delivery device from the skin.

15 Claims, 17 Drawing Sheets

(51) Int. Cl.
*A61M 5/158* (2006.01)
*A61M 5/32* (2006.01)

(52) U.S. Cl.
CPC ............. *A61M 2005/14256* (2013.01); *A61M 2005/1581* (2013.01)

(56) References Cited

U.S. PATENT DOCUMENTS

| | | |
|---|---|---|
| 6,500,150 B1 | 12/2002 | Gross et al. |
| 6,824,529 B2 | 11/2004 | Gross et al. |
| 6,843,782 B2 | 1/2005 | Gross et al. |
| 7,967,795 B1 | 6/2011 | Cabiri |
| 8,152,779 B2* | 4/2012 | Cabiri ............... A61M 5/14248 604/137 |
| 9,149,575 B2 | 10/2015 | Cabiri |
| 2005/0027255 A1 | 2/2005 | Lavi et al. |
| 2009/0093792 A1 | 4/2009 | Gross et al. |
| 2013/0204191 A1 | 8/2013 | Cindrich et al. |
| 2013/0253434 A1 | 9/2013 | Cabiri |
| 2014/0163526 A1 | 6/2014 | Cabiri et al. |
| 2014/0171881 A1 | 6/2014 | Cabiri |
| 2015/0088071 A1 | 3/2015 | Cabiri |
| 2016/0175515 A1* | 6/2016 | McCullough ........... A61M 5/00 604/65 |
| 2016/0184512 A1* | 6/2016 | Marbet ................. A61M 5/158 604/156 |
| 2016/0213840 A1* | 7/2016 | Schabbach .......... A61M 5/3287 |

FOREIGN PATENT DOCUMENTS

| | | |
|---|---|---|
| JP | 2016530016 | 9/2016 |
| WO | 2006052737 A1 | 5/2006 |
| WO | 2011101378 A1 | 8/2011 |
| WO | 2013115843 A1 | 8/2013 |
| WO | 2014179117 A1 | 11/2014 |
| WO | 2014194183 A2 | 12/2014 |
| WO | 2015048791 A1 | 4/2015 |
| WO | 2015048803 A2 | 4/2015 |
| WO | 2015091758 A1 | 6/2015 |
| WO | 2015118358 | 8/2015 |
| WO | 2015118358 A1 | 8/2015 |

OTHER PUBLICATIONS

Int'l Preliminary Report on Patentability dated Nov. 9, 2018 in Int'l Application No. PCT/US2016/056238.

* cited by examiner

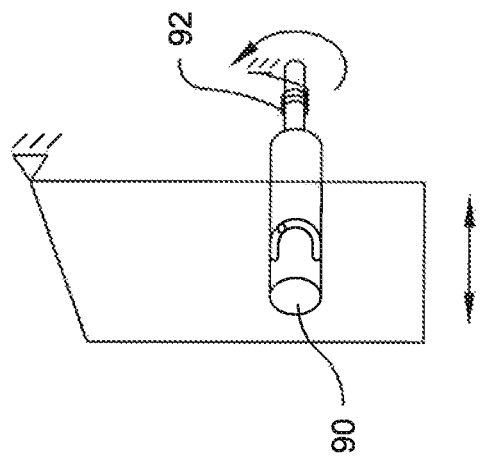
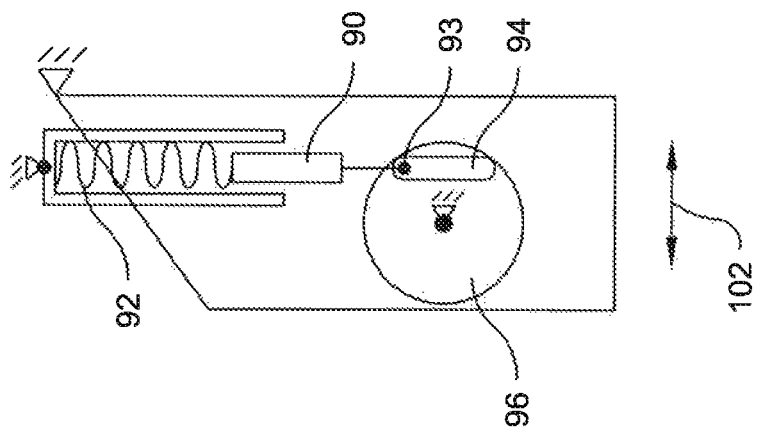

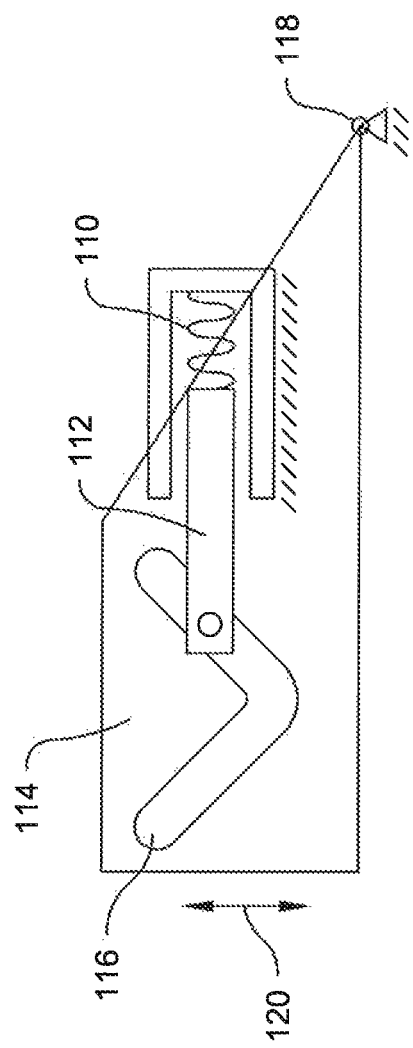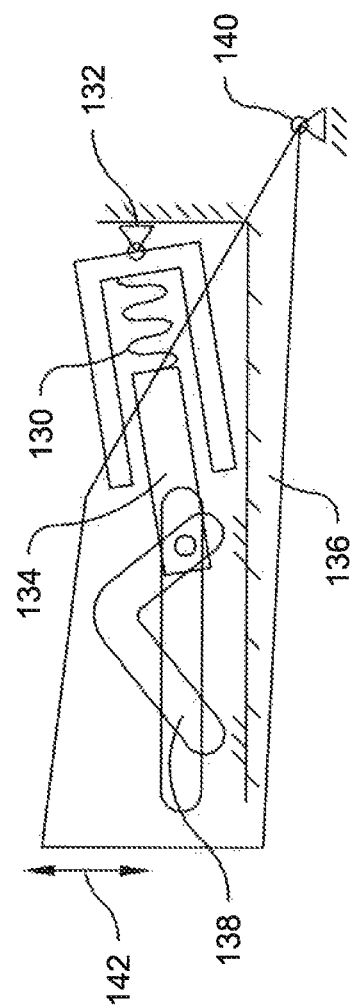

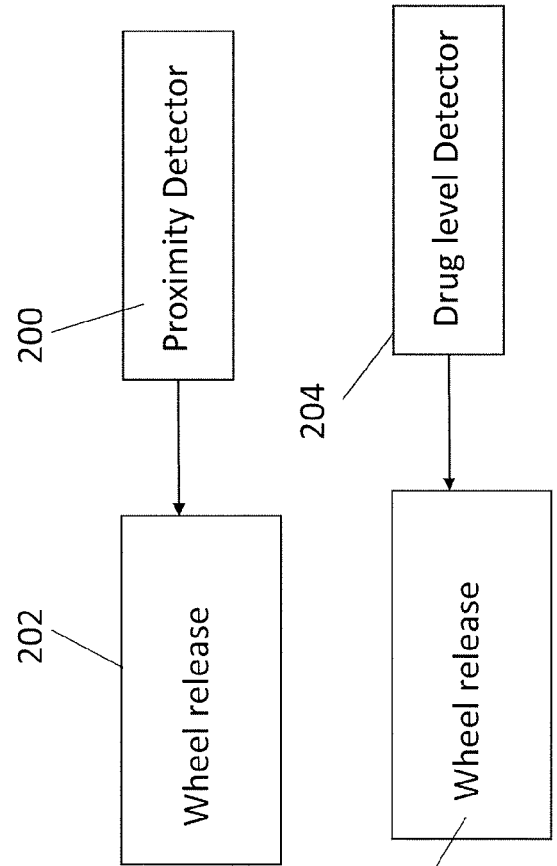

NEEDLE INSERTION AND RETRACTION MECHANISM

CROSS-REFERENCE TO RELATED APPLICATION

This application is a section 371 of International Application No. PCT/US16/56238, filed Oct. 10, 2016, which was published on Apr. 19, 2018 under International Publication No. WO 2018/070978 A1, the disclosure of which is incorporated herein by reference.

FIELD AND BACKGROUND OF THE INVENTION

The present invention, in some embodiments thereof, relates to a needle insertion and retraction mechanism for a syringe and/or drug delivery device and more particularly but not exclusively to such a mechanism for a drug delivery device with a bent tip syringe.

A drug delivery device with a bent tip syringe is a device that contains a substance to be injected and which is placed flat against the skin. A needle is extended perpendicularly from the base of the device against the skin to pierce the skin and inject the drug.

U.S. Pat. No. 6,500,150 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,824,529 discloses "a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,843,782 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 5,858,001 discloses "A liquid drug delivery device" . . . "adapted to be adhered to the skin of a subject by a base member defining a skin-contacting surface having an adhesive coating. A columnar cartridge serves as reservoir for the drug and is incorporated in a housing which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject."

U.S. Patent Publication No. 20140163526 discloses that, "an automated injection device may be loaded with a standard type syringe and/or hypodermic needle. Optionally the syringe may be supplied loaded with medicine and/or covered with a sterile needle cover. The syringe may be loaded into the injector with in a sterile state with needle cover in place. Injector may include for example a fastener (for example an adhesive base). In some embodiments, the fastener may assist a user to hold injector steady on the skin of a patient for an extended period. For example, injector may be used to give injections of volume ranging between 0.5 and 3.0 ml over a time period ranging between 30 sec to 180 sec."

U.S. Patent Publication No. 20150088071 discloses an activation mechanism and a safety latch. The activation mechanism is operative to deploy a needle to protrude out of a housing, the needle having a longitudinal axis. The safety latch is movably mounted on the housing and formed with a needle opening to allow the needle to pass therethrough. The safety latch has a first position wherein the needle is aligned to pass through the needle opening and a second position wherein the safety latch is moved with respect to the housing such that the needle is blocked from movement in a direction parallel to the longitudinal axis thereof by a portion of the safety latch distanced from the needle opening.

International Published Patent Application 2015048791 discloses a method of preparing a compound device for use. The device may include a sealed component and an active outer surface. The outer surface may be protected by a surface cover. Preparing the device may include activating the active outer surface by removing the surface cover and exposing an internal portion of the sealed component to the exterior of the device by unsealing the sealed component and synchronizing the activating and said unsealing using a coupler attached to the surface cover and the sealed component.

International Patent Publication No. 2013/115843 discloses an apparatus for autonomous variable rate delivery of a substance. In some embodiments, the delivery apparatus may be programmable. In some embodiments, the delivery apparatus may be disposable. Optionally the rate of delivery may be dependent on a temperature of a component of the apparatus. Optionally, there may be a time delay between activation of the apparatus and delivery of the substance.

Additional background art includes U.S. Pat. No. 6,189,292. U.S. Patent Publication No. 20130253434, U.S. Patent Publication No. 2009/093,792, U.S. Pat. No. 7,967,795.

The skin contacting surface is intended to make the devices easy for self-administration of the drug. The surface is placed against the skin and a button is pressed or lever released to release a needle to be inserted under the skin. Insertion of the needle is thus straightforward enough to be carried out by the patient alone. However, in practice, many patients find it challenging to insert a needle under the skin and release of the catch generally requires some effort as the needle is released against a restoring force, usually a spring intended to retract the needle after use. The present embodiments relate to the issue of improving ease of use in what is often a psychologically charged operation.

SUMMARY OF THE INVENTION

The present embodiments relate to an insertion and retraction mechanism for an injection needle for the device, wherein the mechanism operates via a single source of tension to power both the insertion and retraction movements. As a result, pressing of the button or release catch is not carried out against any opposing tension and thus is easier for an unskilled user to operate.

In embodiments, the insertion and retraction mechanism may be an axially tensioned rotary part such as a wheel or ratchet or other rotating part that rotates automatically with the tension by pressing a button after the injector device is aligned with the skin. One press may rotate the wheel or ratchet with the tension, or release the wheel with the tension, to extend the needle to pierce the skin, and a second action retracts the needle with a continuation of the same rotation under a continuation of the same tension. The second action may be automatic and connected with removal of the device from the user's skin or with completion of delivery of the drug.

The wheel or ratchet may be operated by a clockwork mechanism, typically based on a tensioned element such as a coiled spring. A tensioning mechanism such as a ratchet may be provided to allow the mechanism to be tensioned for use.

In an embodiment, third and subsequent releases do not cause any reaction from the mechanism, ensuring that the needle is not extended from the device after the drug has been released.

That is to say, in embodiments, the insertion and retraction are two translated parts of an interrupted continuous motion from a tension source which may be a linear or a rotary motion. The tension source may be a leaf spring or a coiled spring and may turn a wheel or press a plunger or otherwise operate the needle for extension and retraction.

In an embodiment, the button is a separate component from the device housing, so that the housing shields the button from accidental pressing, thus adding safety to the device.

According to an aspect of some embodiments of the present invention there is provided a needle insertion and retraction mechanism for a drug delivery device, comprising:

a motion source;

a control for the motion source;

an interrupter for stopping motion of the motion source at a predetermined location and thereby dividing the motion into a first motion part and a second motion part, the second motion part being in continuity with the first motion part;

a motion translation mechanism connecting the source of continuous motion to a needle, the motion translation mechanism configured to extend the needle during the first motion part and to retract the needle during the second motion part.

In an embodiment, the continuity of the motion is angular continuity and the source of continuous motion comprises a tensioned rotator.

In an embodiment, the tensioned rotator comprises a wheel.

In an embodiment, the tensioned rotator comprises a coiled spring, the coiled spring being connected to unwind the wheel about an axis thereof.

In an embodiment, the user operated control is configured to release the source of continuous motion into the first motion part.

In an embodiment, the user operated control is further configured to release the interrupter to cause the second motion part.

An embodiment may comprise a proximity detector configured to detect skin proximity and to release the interrupter to cause the second motion part on detecting of removal of the device from the skin.

An embodiment may comprise a latching mechanism for preventing extension of the needle except in the presence of skin, the latching mechanism comprising a lever having an arm, the lever extending at a predetermined angle below a base of the drug delivery device to insert the arm to prevent motion of the user-operated control, to render the user-operated control inoperable, the lever being displaceable from the predetermined angle by the presence of skin of the user, thereby moving the arm and releasing the user-operated control.

An embodiment may comprise an adhesive layer below the base to adhere the drug delivery device to skin of the user, removal of the drug delivery device from the skin and against the adhering causing a pulling force on the base, the pulling force causing release of the interrupter to cause the second motion part.

An embodiment may comprise a drug level detector configured to detect a level of a drug being administered by the device and to release the interrupter to cause the second motion part on detecting completion of administering the drug.

In an embodiment, the drug level detector comprises a position detector for detecting a position of a plunger pushing the drug being administered into the needle.

In an embodiment, the continuity is linear.

In an embodiment, the first and second motion parts are due to successive releases of a single tension source.

In an embodiment, the single tension source comprises a coiled spring.

An embodiment may comprise a tensioning mechanism for allowing external tensioning of the motion source.

In an embodiment, the motion source is a coiled spring and the tensioning mechanism is a winding mechanism.

An embodiment may comprise a latching mechanism for preventing extension of the needle after the needle has been retracted.

In an embodiment, the motion source is connected to an external winding mechanism for priming prior to use.

According to a second aspect of the present invention there may be provided a method, the method involving:

releasing a tensioned motion source, the motion source having a continuous movement including a first motion part and a second motion part, the motion source being released to carry out the first motion part;

translating the first motion part into an extension motion of a needle;

releasing the tensioned motion source to carry out the second motion part, the second motion part being direction-wise continuous with the first motion part; and translating the second motion part into a retraction motion of the needle.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A, 4B and 4C are simplified diagrams showing a linear plunger operating a cam according to an embodiment of the present invention;

FIG. 5 is a simplified diagram showing an alternative embodiment of a linear plunger operating a cam;

FIG. 6 is a simplified diagram showing a second alternative embodiment of a linear plunger operating a cam;

FIG. 15 is a simplified diagram showing an embodiment of the present invention using a proximity sensor to detect the end of an injection process;

FIG. 16 is a simplified diagram showing an embodiment of the present invention using a drug level detector to determine when the drug injection is complete;

FIG. 17 is a simplified diagram showing an embodiment of the present invention using a position detector to detect the position of the syringe plunger to determine when the drug injection from the device is complete;

DESCRIPTION OF SPECIFIC EMBODIMENTS OF THE INVENTION

Figure 1:
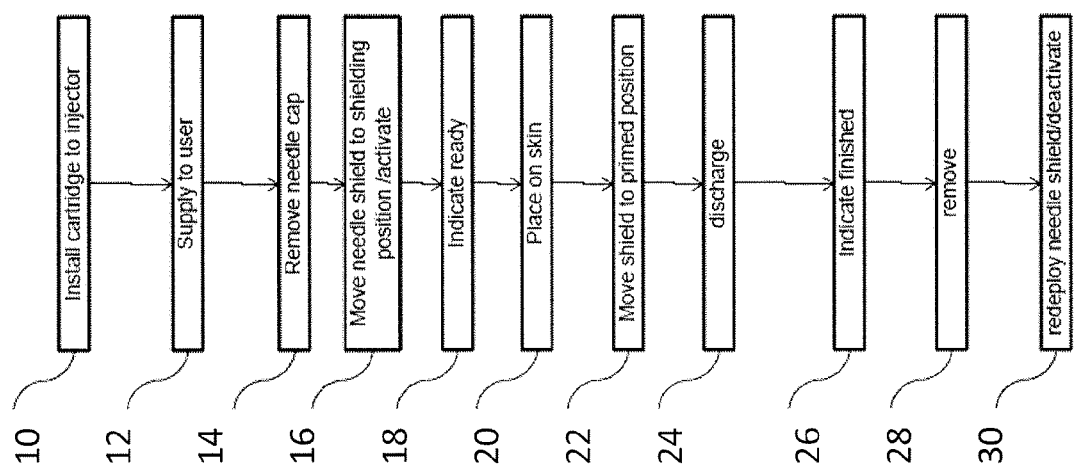
FIG. 1 is a simplified flow chart showing general operation of an injection device according to the present embodiments.

The present invention, in some embodiments thereof, relates to an injection mechanism and, more particularly, but not exclusively, to a mechanism for extending an injection needle in a syringe or other drug delivery device.

A needle insertion and retraction mechanism for a drug delivery device, comprises a motion source, a user-operated control for the motion source, and an interrupter for stopping motion of the motion source at a predetermined location and thereby dividing the motion into two parts which are continuous relative to each other. A motion translation mechanism connects the source of continuous motion to a needle, to extend the needle during the first motion part and to retract the needle during the second motion part. The needle is thus extended and retracted by continued operation of a single tension source rather than two tension sources operating in opposition to each other.

In an embodiment, the user activation mechanism is made up of a button, which is a separate component from the device housing. In an embodiment, the housing shields the button from accidental pressing, thus providing a two stage activation system and adding safety to the device. A latch may also be provided to latch the button, the latch being released by placing the drug delivery device in proximity to the skin.

In use the drug delivery device may be adhered to the skin, in particular for slow injection operations that require the injected material to be dispensed over a predetermined period of time that is longer than the time it is easy to hold the delivery device steady. In such a case, withdrawal of the adhered device after the injection is over may exert a force through the base of the device which can be detected to operate the second motion part and withdraw the needle.

The drug delivery device is now considered in general. A drug syringe and/or drug reservoir may be provided with a needle protruding from the syringe at an angle to the axis of the barrel of the syringe. Optionally the syringe may include a hub with a mount for a needle cap and/or a needle fitting and/or a luer fitting; for example the hub may be at an angle to the axis of the barrel of the syringe. Optionally the syringe or reservoir is configured to be pre-filled with a drug for injecting via the needle. Optionally the hub includes a built in needle and/or a needle mount and/or a mount for a sterile needle cap at an angle to the axis of the barrel of the syringe.

In some embodiments, the user removes a sterile needle cap from the prefilled sterile syringe before use. Optionally removing the needle cap activates the device and/or peels an adhesive cover and/or triggers deployment of a needle shield latch from an open position to a shielding position. In some embodiments, placing a base of the device on the skin of a subject moves the needle shield latch into a primed position. Optionally, the device discharges a drug into the subject with the axis of the prefilled syringe substantially parallel to the base of the device and/or the skin of the subject. Optionally a needle mounted on the cartridge may be inserted into the skin of the subject and/or may serve as a fluid path directly from the cartridge to the subject. Optionally, removing the device from the skin of the subject redeploys the needle shield latch and/or deactivates the device. The present embodiments relate in particular to the extension and retraction of the needle.

In some embodiments the drug delivery device may include a prefilled syringe and/or reservoir with a needle and/or hub at an angle to the axis of the barrel of the reservoir for example as described in various embodiments herein. For example, the drug delivery device may include a needle shield and/or a safety latch and/or a needle retraction mechanism for example as described in various embodiments herein. For example, the delivery device may include a needle cap and/or cover remover for example as described in various embodiments herein. For example, the delivery device may include a dual movement pivot for example to insert a needle into the subject as described in various embodiments herein.

The needle needs to be both inserted and removed in a way that is simple for the user. The insertion is linear and so is the removal and one way to achieve both insertion and removal is to have two springs or like sources of tension working against each other, or to insert the needle with the press of a button against the tension of a spring intended to facilitate withdrawal of the needle.

In either case, the patient is required to press hard in order to insert the needle, since the pressing action requires extending the needle against the tension of the spring intended for withdrawal. This may be difficult psychologically, and also may be problematic if the device is going to be used against soft tissues, as the user may inadvertently push the device, inadvertently pushing the tissues aside and causing the needle to be inserted otherwise than intended.

The present embodiments may thus use a single source of tension to operate both the insertion and retraction of the needle. One embodiment may use a rotating member to carry the single source of tension about its axis of rotation and to insert and extract the needle over the course of the two parts of a full rotation. The rotating member has an initial position with the needle extracted, a first rotated position which extends the needle from the device and a second rotated position in which the needle is withdrawn. Axial tension may pull the rotating member from one position to the next each time a release action is carried out by the user, such as pressing a button.

In the present embodiments, the forces are local. The base pulls the cover during insertion and pushes during retraction, and thus the only force that the user is involved with is the button pressing force, which may be accurately calibrated in the present design.

The force to raise and lower the cover may also depends on the coiled spring which, again may be accurately calibrated using the present design. Thus the needle insertion force and velocity may be controlled.

In the present embodiments, the states (A. ready, B. injection. C. locked end) may be well defined, thus obviating the need for any intermediate position or state.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a flow chart illustration of a method of delivering a drug and/or shielding a needle in accordance with an embodiment of the current invention. Optionally a single use drug delivery device, for example an injector, such as an auto-injector or a patch injector, a bolus injector and/or a body worn injector, may come preloaded with a drug. For example the device may include a cartridge. Optionally the cartridge includes a sterile syringe with a hub and/or sterile needle mounted at an angle to the axis of the syringe barrel. The syringe is optionally prefilled with a drug. Optionally the device may include a needle shield latch and/or a status indicator. Optionally the device may include an attachment mechanism, for example an adhesive for attaching to a subject.

In some embodiments a cartridge may be installed 10 to the delivery device before assembly and/or before being shipped to a retailer and/or a health provider and/or a user. Alternatively or additionally the cartridge may be installed 10 into the drug delivery device by a user, for example a health provider (for example a nurse and/or a pharmacist and/or a doctor and/or a health aid) and/or a subject of the injection (e.g. a patient receiving the drug) and/or a caretaker.

In some embodiments an assembled injector (with the cartridge installed 10) may be supplied 12 to a user. Optionally as supplied 12 to the user, the cartridge and/or hub and/or the needle may be sterile and/or covered with a sterile needle cap. Optionally, the auto-injector may have a needle shield latch. For example, while the needle cap is in place the needle shield latch may be in an open position, allowing the access to the needle cap. For example, when the needle shield latch is in the open position there may be space for the cap and/or a cap remover to protrude out of the auto-injector. For example, in the open position, the needle shield latch may retract. In some embodiments the needle shield latch may pivot and/or slide from one position and/or state to another. Alternatively or additionally the cartridge and/or the injector may be supplied 12 to the user separately and/or may be assembled by the user.

In some embodiments, before use of an injector, the needle cap may be removed 14. For example, the needle cap may be pulled off of the cartridge through an aperture in the injector housing. Optionally removing 14 the needle cap may cause the delivery device to be activated 16 and/or the needle shield to move to a shielding position. For example, the cap and/or a removal tool may be connected to a switch and/or a battery insulator and/or an adhesive protector. Removing the cap optionally activates the switch and/or causes removal of the battery insulator and/or removal of the adhesive protector. Once activated 16, the delivery device optionally indicates 18 that it is ready to be placed on a subject. Optionally, once the needle shield is in the shielding position it may prevent replacement of the needle cap. Optionally, when the needle shield is in the shielding position it may prevent exposure of the needle. For example, in the shielding position, the needle shield may block the needle tip from extending out of the injector. Alternatively or additionally, when the shield is in the shielding position the needle extension mechanism may be locked and/or disabled thereby preventing extension of the needle out of the injector and/or in the shielding position the needle shield may shield an extended needle tip.

In some embodiments, the injector is placed 20 on the skin of a subject. For example, the delivery device may be placed 20 on the skin of the subject after activation 16. Optionally placement on the skin causes the needle shield to move 22 to a primed position. For example, the shield may be pushed by the skin of the subject into the primed position. Movement 22 of the shield into the primed position may cause extension of a needle from the injection device and/or insertion of the needle through the skin of the subject. For example, the shield may collapse inward exposing the needle and/or allowing the needle to enter the subject and/or movement 22 of the shield may trigger an insertion mechanism. Alternatively or additionally, movement 22 of the shield into the primed position may open a path for the needle to exit the injector. For example, movement 22 of the shield into the primed position may align a hole in the shield to the needle allowing the needle to be extended out of the device, for example through the hole in the needle cap. Alternatively or additionally, an additional step may cause insertion of the needle, for example pushing a button and/or pushing a portion of the injector towards the skin of the subject.

After insertion of the needle, a drug may be delivered 24 into the subject. For example the needle may be hollow and the drug may be delivered 24 through the needle into the subject. Optionally, once injection has completed the device may indicate 26 that injection is finished and/or that the device may be removed. Optionally when a malfunction occurs (for example an occlusion of the fluid path) an indicator may indicate that a malfunction has occurred and/or that the injector should be removed. In some embodiment, the needle may retract upon completion of injection and/or upon certain malfunctions. Alternatively or additionally, the needle may remain extended after delivery 24.

In some embodiments, after delivery 24 and/or error and/or when indicated to do so, a user may remove 28 the injector from the skin of the subject. In some embodiments when the injector is removed 28, the needle shield may redeploy 30. Redeployment 30 of the needle protector may protect the needle and/or shut down the device. Alternatively or additionally, needle retraction may protect the needle. Alternatively or additionally, the device may shut down and/or be disabled immediately after completion of delivery 24 and/or upon certain malfunctions. Alternatively or additionally, the device may shut down and/or be disabled after a certain time period after the completion of delivery 24 and/or upon certain malfunctions.

Figure 2A:
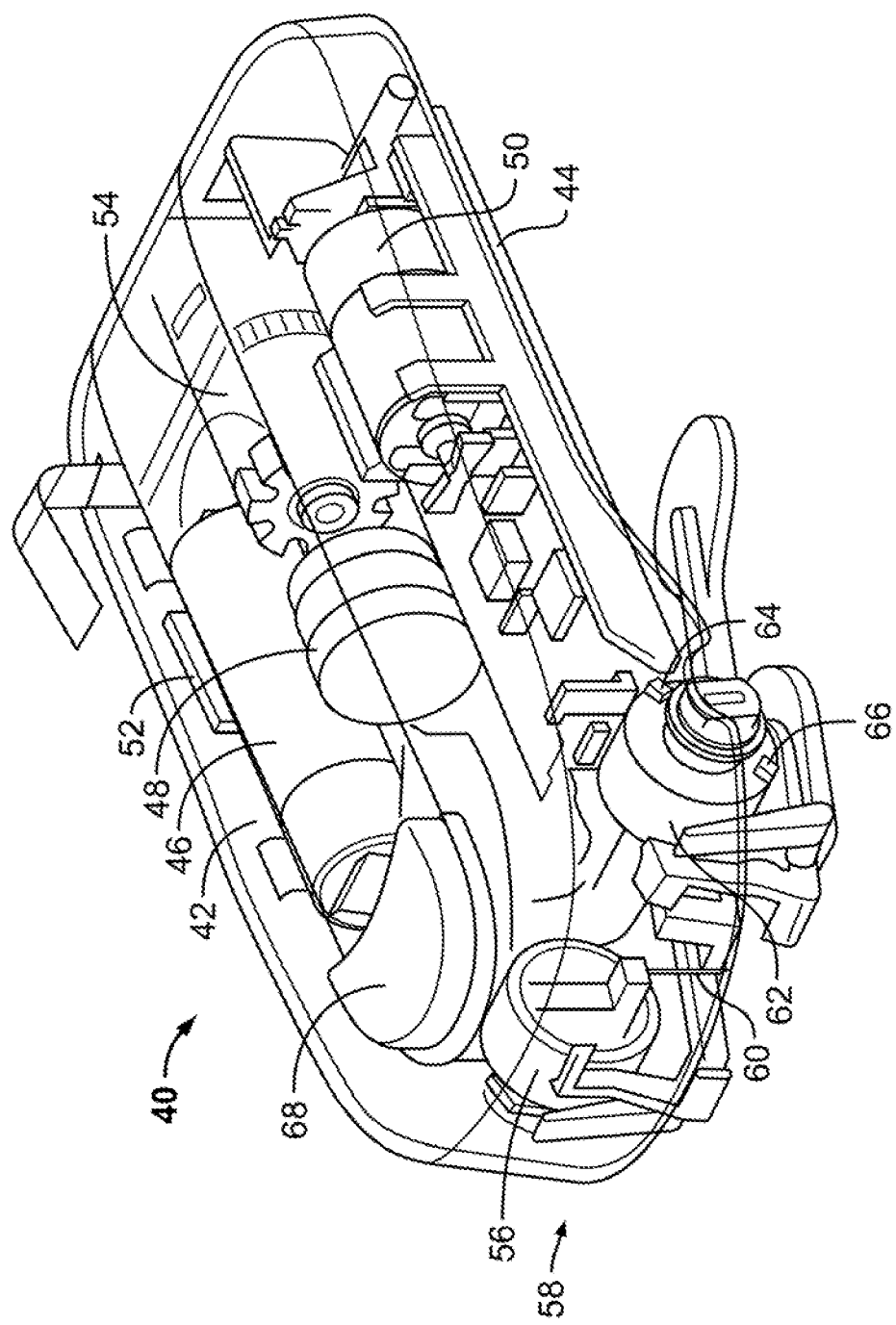
FIG. 2A is a simplified diagram showing an injection device according to the present embodiments.

Reference is now made to FIG. 2, which is a simplified diagram illustrating a drug delivery device 40. The drug delivery device includes upper and lower longitudinal surfaces 42 and 44, wherein lower longitudinal surface 44 is intended to be placed against the skin. Reservoir 46 contains a drug to be injected and plunger 48 empties the drug into the needle for injection. The plunger is operated by a plunger operation mechanism including a small electric motor 50 and battery 52, and a motion translation arrangement 54. A needle insertion mechanism 56 is located at a forward end 58 of the drug delivery device 40 to insert needle 60 into the skin of a patient and withdraw the needle afterwards.

A motion source may be provided to operate the needle 60. The motion source may in one embodiment be a tensioned wheel 62. In other embodiments a plunger may be pushed by a spring. The tensioned wheel may comprise two lugs 64 and 66 which interrupt the motion of the wheel.

A user-operated control for the motion source may comprise button 68. As the button is pressed once, the first lug 64 is released, allowing the wheel to rotate half a turn. The motion of the half turn is translated into an insertion motion for needle 60, thus inserting the needle. In an embodiment, the button 68 is a separate component from the device housing, so that the housing shields the button from accidental pressing. To reach the button, the cover part of the housing may be lowered, thus providing a two stage activation system and adding safety to the device.

The second lug 66 then serves as an interrupter, stopping motion of the wheel at a preset location at which the insertion motion of the needle is complete. The second lug thus divides the wheel motion into a first motion part and a second motion part, the two motion parts being in continuity with each other.

A second wheel may be provided on the other side of the button, not visible in the present figure, to provide more balanced motion.

As the wheel is released a second time, it rotates from the second lug to the first lug on the second part of a complete rotation, and the motion is translated into retraction of the needle.

In an alternative embodiment, the needle may not be retracted, but rather the base may extend to shield the needle when the device is removed from the skin.

Alternatively or additionally, the linear movement of the needle retraction may for example be by means of multiple actuators or springs moving the needle in opposite directions. In some embodiments, the activation button may return to the original position and/or be locked after injection.

Alternatively or additionally, needle retraction may be activated by a switch. For example there may be a needle retraction switch and/or after needle insertion the activation button may be reused as a needle retraction switch.

A motion translation mechanism to be discussed in greater detail below, connects the wheel or any other source of the continuous motion to the needle 60. The motion translation mechanism may insert the needle during the first motion part and may retract the needle during the second motion part.

In the case of a wheel as the motion source, the continuity of the motion is angular.

As will be discussed below, instead of or in addition to a wheel with lugs, a suitably shaped cam may be used.

Figure 2B:
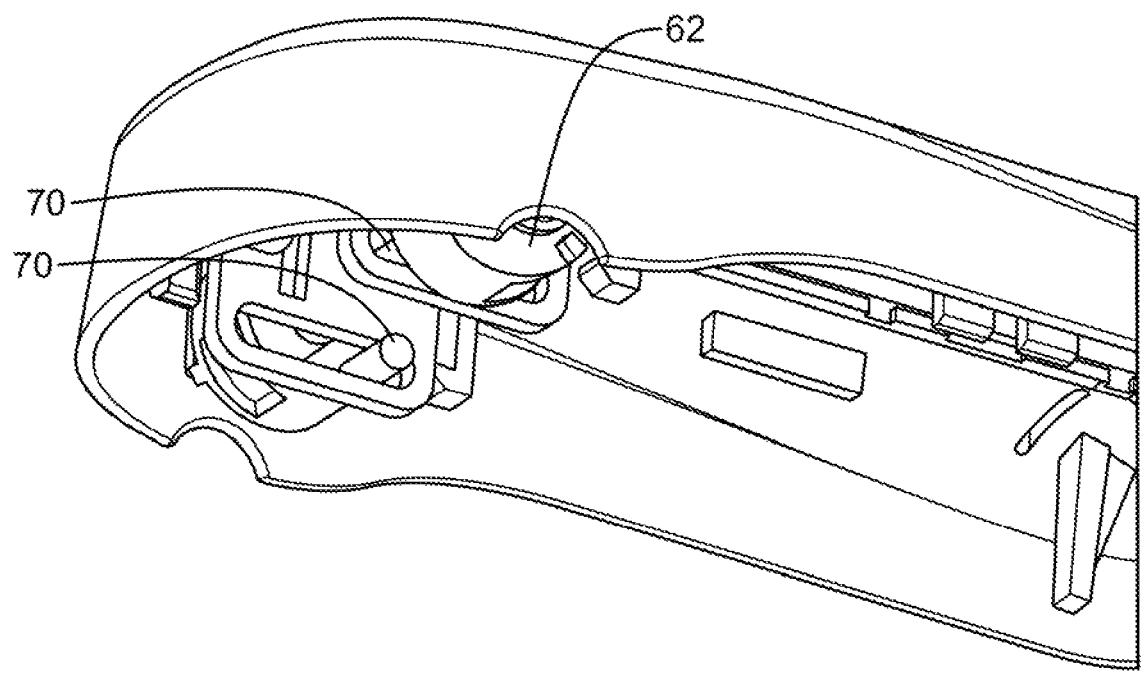
FIG. 2B is simplified diagram showing a view from below of the injection device of FIG. 2A with the needle removed.

Reference is now made to FIG. 2B, which is a simplified diagram showing how the wheels are connected to the cover of the device 40, via pin 70.

Lugs 62 and 64 are optional and may be omitted in some embodiments. However an element is required which is responsible to prevent the cover from being lowered prior to use. Such an element may be a contact between the button and the structure (base/cover) or the wheel lug 62, 64 or the pin 70. A second element or contact is responsible for preventing movement when the wheel is held in the lower or extended position. Again the feature may be provided by the contact between the safety latch lug and wheel pin. A third element/contact is responsible for arresting motion at the end of travel, thus ensuring that the needle, once retracted, cannot be extended again. Such a feature may be provided by contact between the wheel lug or wheel pin and the structure.

Figure 3:
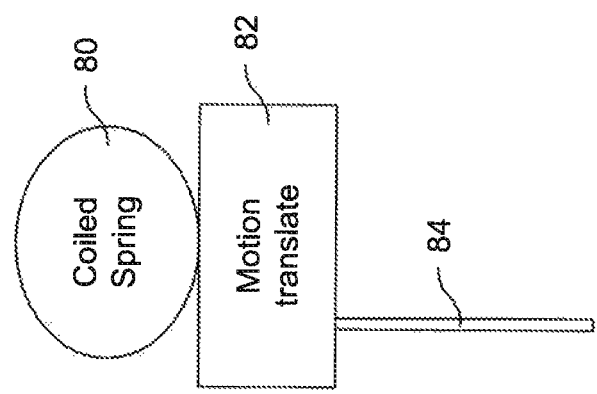
FIG. 3 is a simplified diagram showing a coiled spring providing motion which is translated into needle extension and retraction according to an embodiment of the present invention.

Reference is now made to FIG. 3, which is a simplified diagram showing an embodiment in which the motion source is a coiled spring 80 connected directly to a motion translation unit 82. The motion translation unit comprises a series of levers which translate the rotary uncoiling of the spring 80 into a lowering and a raising part motion of the needle 84. That is to say, as the spring uncoils, the motion is divided into two parts, one translating into a first direction and the other translating into a second opposite direction.

Figure 4A:
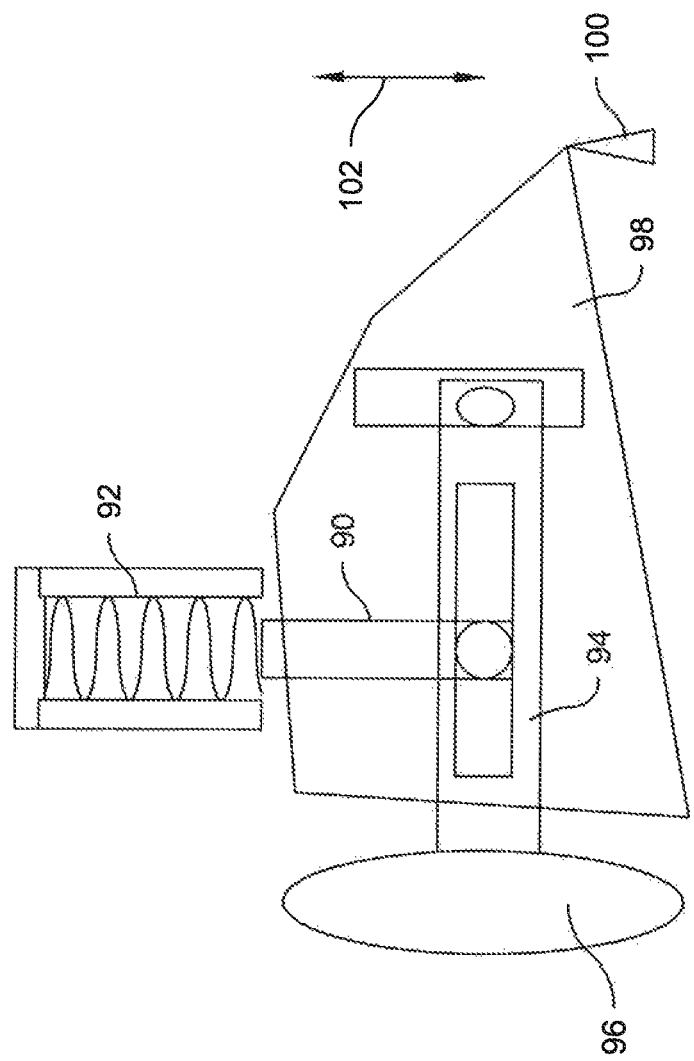

Reference is now made to FIG. 4A. In FIG. 4A the motion source is a plunger 90 tensioned by coiled spring 92. The plunger is pushed linearly by coiled spring 92 and is pivotally attached to beam 94 which rotates around wheel 96. Beam 94 is pivotally attached to cam 98, which is in turn pivotally attached at pivot point 100, so that initial travel is downwards and subsequent travel is upwards. As the plunger is pushed by the coiled spring, the motion is divided into two parts, one translating into a first direction and the other translating into a second opposite direction, as indicated by arrow 102.

Reference is now made to FIG. 4B which is an alternative embodiment of a motion translation mechanism. Again the motion source is plunger 90 tensioned by coiled spring 92. The plunger is pushed linearly by coiled spring 92 and is pivotally attached at pivot 93 to beam 94, which rotates cam 98. Due to constraints of the fitting, the wheel is turned first one way and then the opposite way, as indicated by arrow 102.

Reference is now made to FIG. 4C, which is another alternative embodiment of a motion translation mechanism. Again the motion source is plunger 90 tensioned by coiled spring 92. The plunger is in this case rotated by coiled spring 92 and has shaped slit 104. Pin 106 rides in the slit—extending in the direction out of the paper and thus turning a wheel in a plane at 90 degrees to the image first in one direction and then in the other direction.

Reference is now made to FIG. 5 which illustrates a variation of FIG. 4 in which a coiled spring 110 operates a plunger 112 to slide pivoted cam 114 over angled beam 116. The cam 114 is pivoted at pivot point 118. As the plunger moves, the motion is divided into two parts, one translating into a first direction and the other translating into a second opposite direction, as indicated by arrow 120.

Reference is now made to FIG. 6, which is a simplified diagram illustrating a variation of the embodiment of FIG. 5. In FIG. 6 coiled spring 130 is itself pivoted at pivot point 132 and operates plunger 134 to push cam 136 against angled beam 138. The cam 136 is pivoted at pivot point 140. As the plunger is pushed, the motion is divided into two parts, one translating into a first direction and the other translating into a second opposite direction, as indicated by arrow 142.

Figure 7:
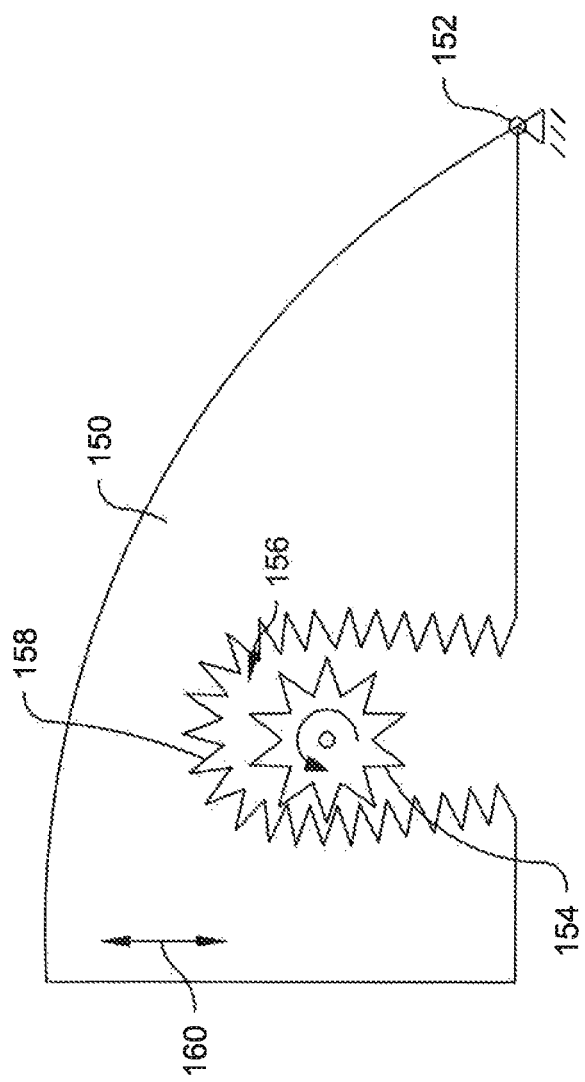
FIG. 7 is a simplified diagram showing a rotating cog operating a cam from inside according to an embodiment of the present invention.

Reference is now made to FIG. 7, which illustrates a further variation of the present embodiments. In FIG. 7 a cam 150 is pivoted at pivot point 152 and a pre-tensioned cog wheel 154 lies inside the cam in a concave intrusion 156 with corresponding teeth 158. As the cog wheel 154 rotates, the motion is divided into two parts, one translating into a first direction and the other translating into a second opposite direction, as indicated by arrow 160.

Figure 8:
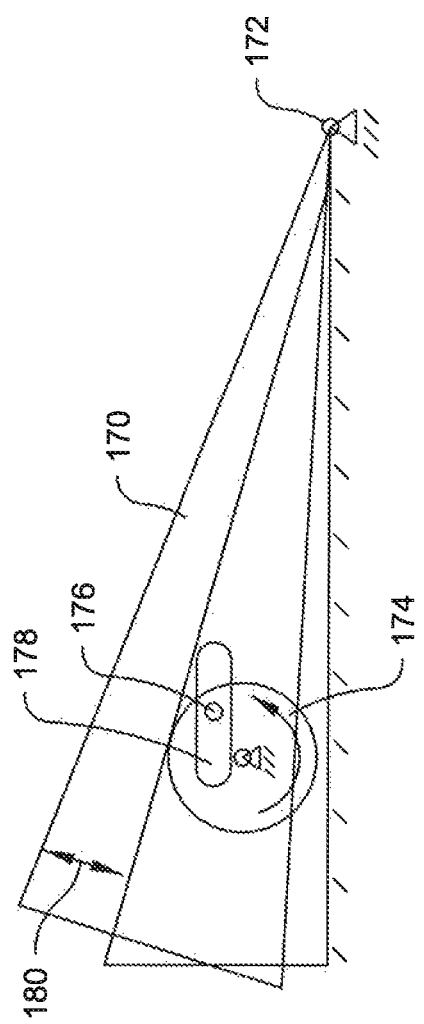
FIG. 8 is a simplified diagram showing a cam operated by a tensioned wheel and suitable for the embodiment of FIG. 2.

Reference is now made to FIG. 8, which is a simplified diagram illustrating a motion translation mechanism for the wheel embodiment of FIG. 2. Cam 170 is pivoted at pivot position 172. Wheel 174 is tensioned by a rotator and has a pivot 176 which moves in slot 178 within cam 170. The cam moves up and down as shown by arrow 180. The wheel is operated by the tensioned rotator which is typically a coiled spring, and the coiled spring unwinds to rotate the wheel about its axis.

Figure 9:
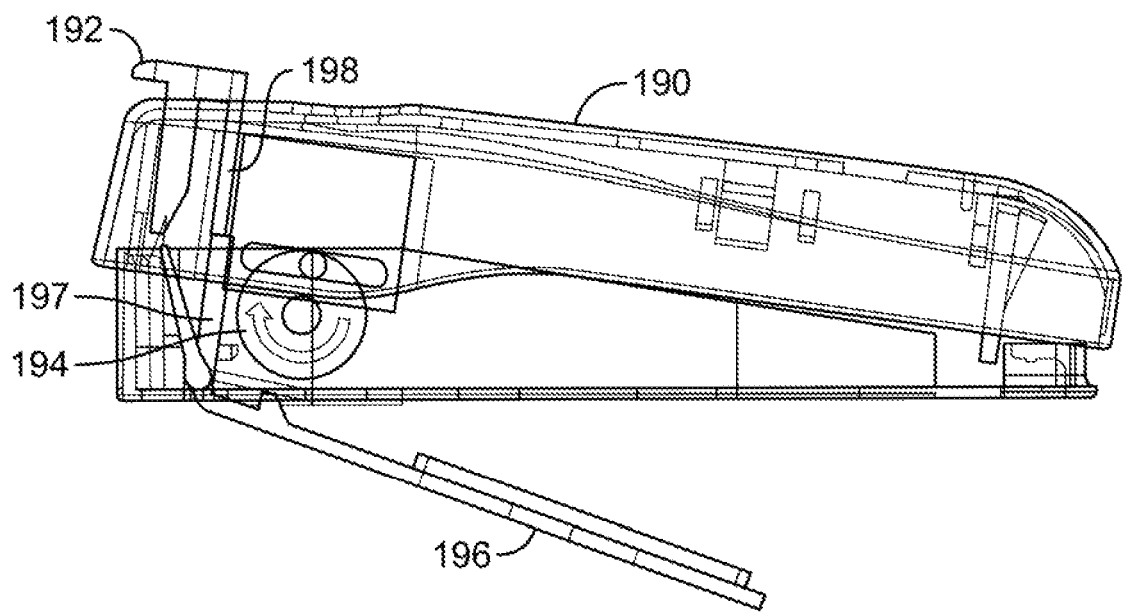
FIG. 9 is a simplified diagram showing a device according to the present embodiments prior to use with the safety latch, button and cover locked.

Reference is now made to FIG. 9, which is a simplified diagram showing a device according to the present embodiments. The device has cover 190, user operable button 192, tensioned wheel 194, and safety latch 196. The device is loaded with drug prior to use and the button and cover are locked so that the button cannot be pressed and the cover cannot be depressed. Specifically the safety latch 196 may block pressing of the button due to arm 197 sitting under button extension 198.

Figure 10:
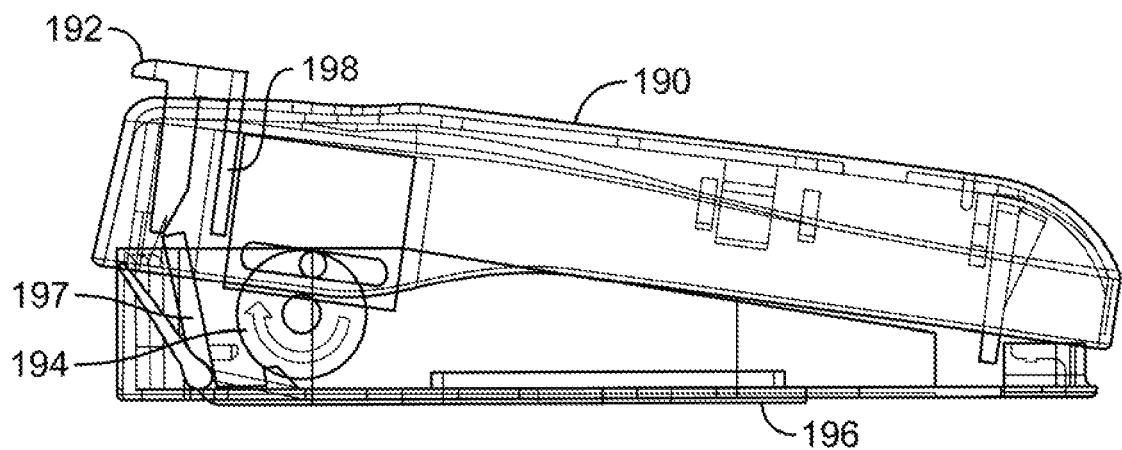
FIG. 10 is a simplified diagram showing the device of FIG. 9 with the safety latch removed, the button released and the cover locked.

Reference is now made to FIG. 10, which is a simplified diagram showing the device of FIG. 9 in a state just prior to use. Parts that are the same as in FIG. 9 are given the same reference numerals and are not described again except as needed for an understanding of the present figure. The device is placed against the skin on the injection site which pushes up the safety latch 196 against the base of the device, thus allowing the button to be pressed. The button is now possible to press because arm 197 has rotated forward and no longer sits under button extension 198. However the cover 190 is still locked although the button can now be pressed to release the needle.

The safety latch thus ensures that the button cannot be pressed unless the injector is placed flush against a flat surface. The safety latch mechanism is not restricted to the present embodiments but is suitable for any kind of injector which is placed flush against the patient's skin. More generally, the safety latch is a latching mechanism for preventing extension of the needle except in the presence of skin, and comprises a lever, namely safety latch 196, having an arm 197, the lever extending at a predetermined angle below the base of the drug delivery device to insert the arm to prevent motion of the user-operated control, namely button 192, to render the button inoperable. The lever is displaced from the predetermined angle shown in FIG. 9 as it is pressed flush against the base by the presence of skin, thereby moving the arm forward and releasing the button.

Figure 11:
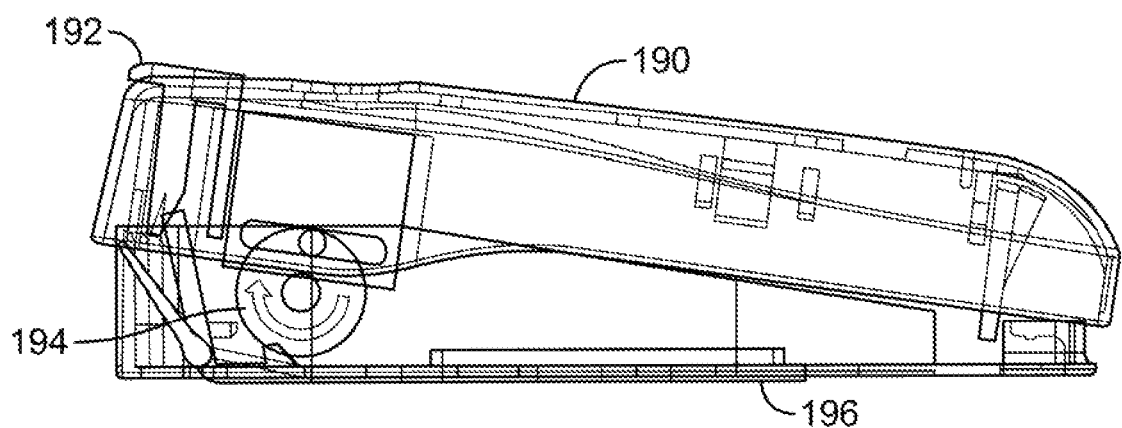
FIG. 11 is a simplified diagram showing the device of FIG. 9 with the button pressed to release the loaded wheel mechanism.

FIG. 11 is a simplified diagram showing the device of FIG. 9 with the button 192 being pressed to insert the needle. Parts that are the same as in FIG. 9 are given the same reference numerals and are not described again except as needed for an understanding of the present figure. The button 192 is pressed and wheel 194 is released to rotate under tension and insert the needle.

Figure 12:
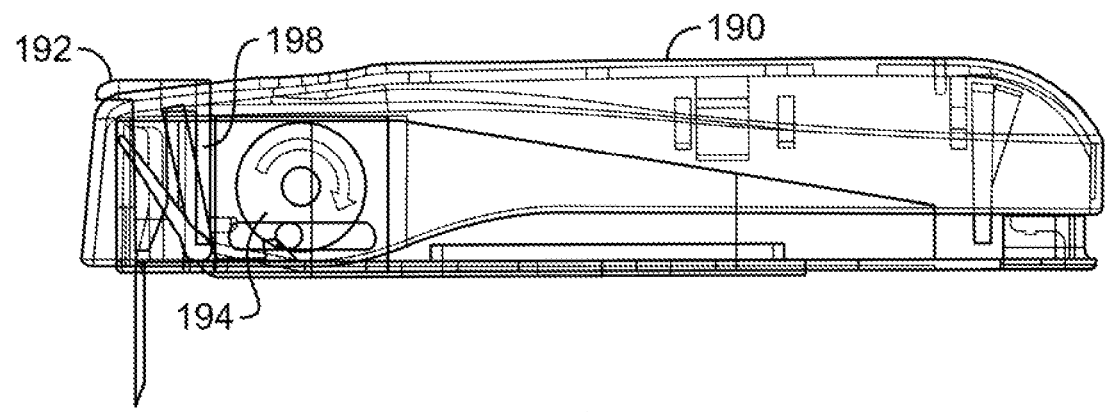
FIG. 12 is a simplified diagram showing the device of FIG. 9 after the needle has been inserted for injection.

FIG. 12 is a simplified diagram showing the device of FIG. 9 after the needle has been inserted for injection. Parts that are the same as in FIG. 9 are given the same reference numerals and are not described again except as needed for an understanding of the present figure. The wheel 194 has rotated by half a rotation and needle 198 is extended from the device so that injection takes place.

Figure 13:
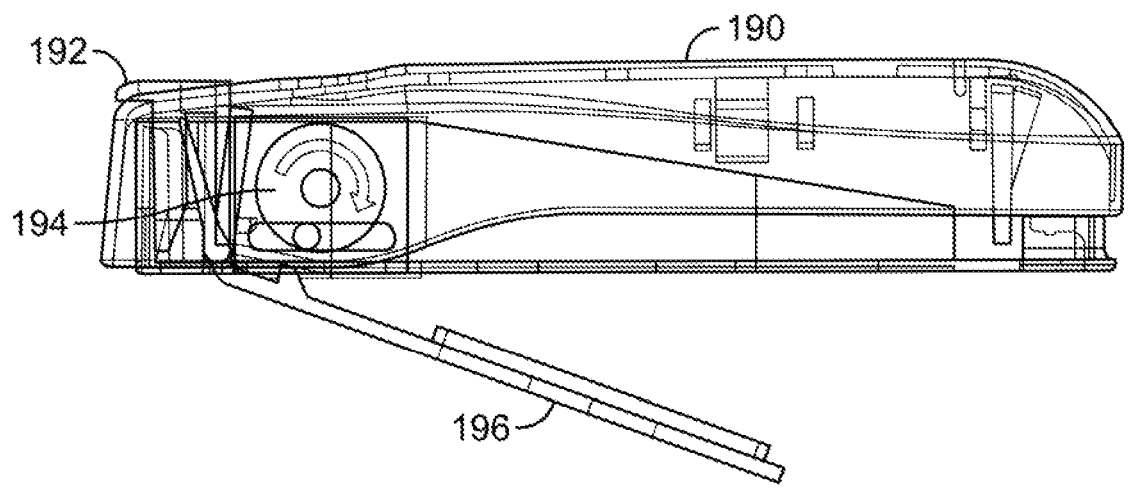
FIG. 13 is a simplified diagram showing the device of FIG. 9 with the safety latch opened to release the wheel for retraction.

FIG. 13 is a simplified diagram showing the device of FIG. 9 with the safety latch opened to release the wheel for retraction. Parts that are the same as in FIG. 9 are given the same reference numerals and are not described again except as needed for an understanding of the present figure. In FIG. 13, as the device is withdrawn from the skin after use, the safety catch 196 extends downwards, releasing tensioned wheel 194 for its second half turn. The half turn withdraws the needle. At the end of the half turn the wheel is arrested so that no further turning is possible.

Figure 14:
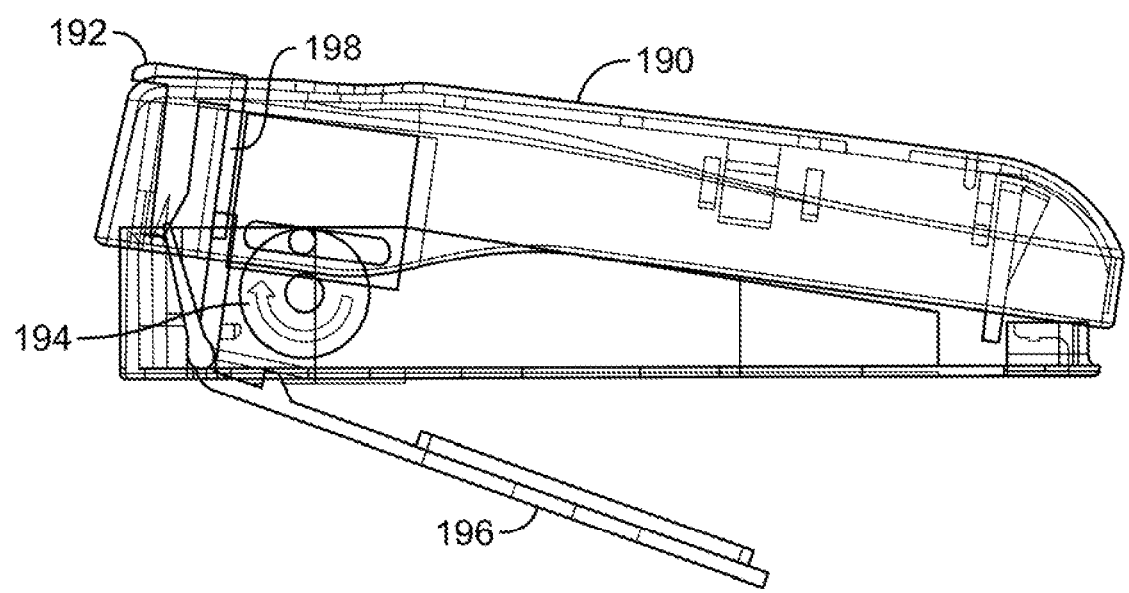
FIG. 14 is a simplified diagram showing the device of FIG. 9 locked after use.

FIG. 14 is a simplified diagram showing the device of FIG. 9 locked after use. Parts that are the same as in FIG. 9 are given the same reference numerals and are not described again except as needed for an understanding of the present figure. In FIG. 14 the cover 190 is raised, again locking the device so that used needle is not exposed.

In the above embodiment, the safety latch acted as a mechanical proximity sensor. Referring now to FIG. 15 a proximity detector 200 may be used to detect skin proximity and to release 202 the wheel, or the interrupter on the wheel, to cause the second motion part on detecting of removal of the device from the user's skin. Thus the retraction of the needle occurs automatically upon removal of the device from the user. As above the proximity sensor was mechanical but an optical or infrared proximity sensor may also be used and electronically actuate the wheel release.

Reference is now made to FIG. 16 which illustrates a further alternative embodiment in which a drug level detector 204 detects a level of a drug being administered by the device and releases the wheel to cause the second motion part on detecting completion of administering of the drug. That is to say, when the reservoir or syringe is determined to be empty then the needle is automatically retracted.

Referring now to FIG. 17 and, in an embodiment, the drug level detector is simply a position detector 206 which detects the position of syringe plunger 48 (FIG. 1) pushing the drug being administered into the needle. When the plunger is determined to be at the end of its travel then it is inferred that the injection process is complete and the wheel is released to carry out the second part of its motion and retract the needle.

Figure 18:
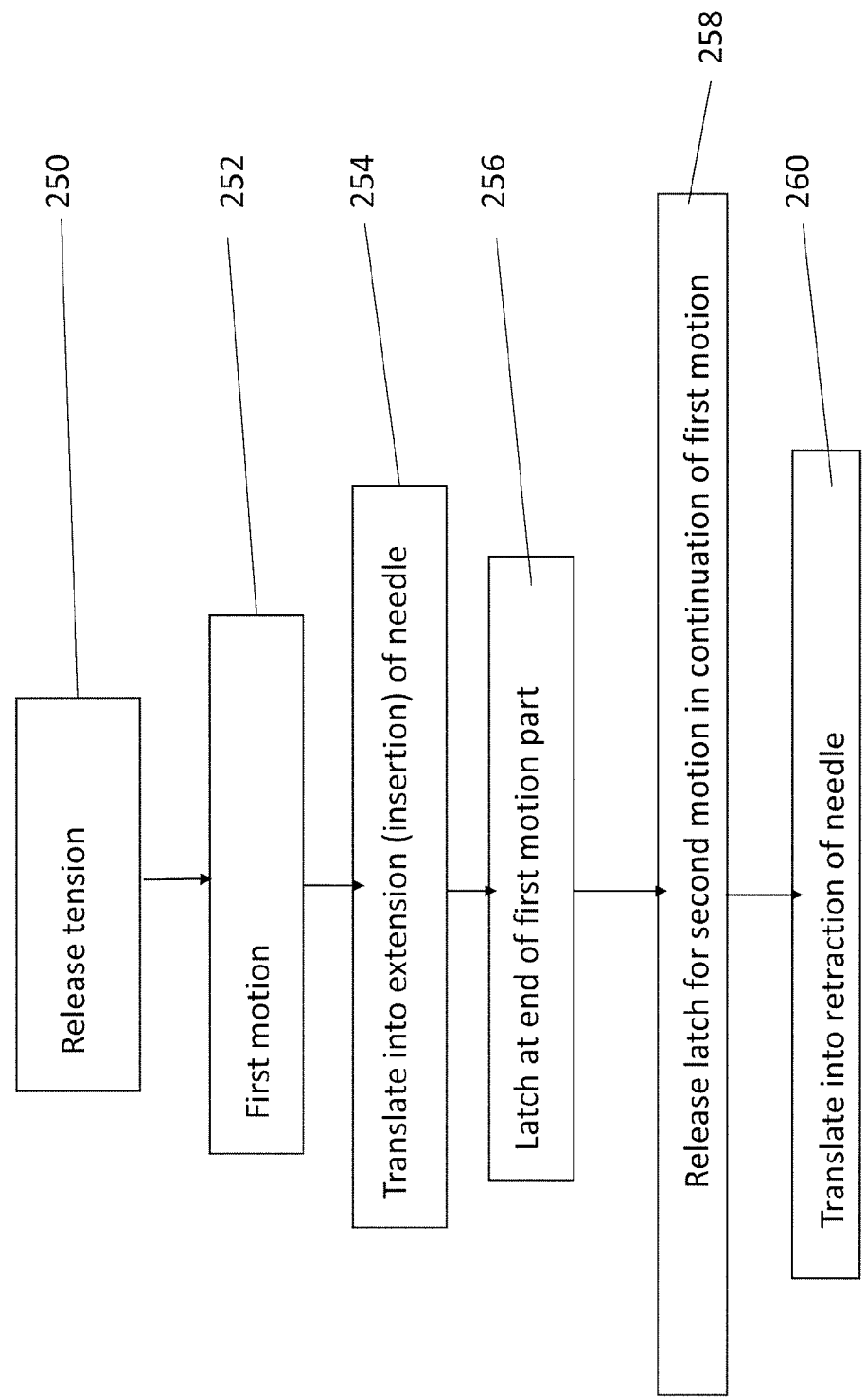
FIG. 18 is a simplified diagram showing a flow chart of needle insertion and retraction according to an embodiment of the present invention.

Reference is now made to FIG. 18, which is a simplified flow chart showing operation of a needle insertion and retraction mechanism of the present embodiments. A method of operating a needle insertion and retraction mechanism comprises:

releasing a tensioned motion source 250 and carrying out a first motion part 252. The first motion part is then translated into an extension motion of the needle—254.

The mechanism is latched to allow the needle to remain in the extended position for the duration of the injection 256 and then the tensioned motion source is released a second time to carry out the second motion part which is continuous with the first motion part—258. The second motion part is then translated into retraction of the needle.

As discussed, where a wheel and a coiled spring that unwinds to rotate the wheel is used, then the first and second motion parts are angularly continuous. In the case of a plunger being pushed in a linear motion the first and second motion parts are linearly continuous. The first and second motion parts may be due to successive releases of the single tension source.

Figure 19:
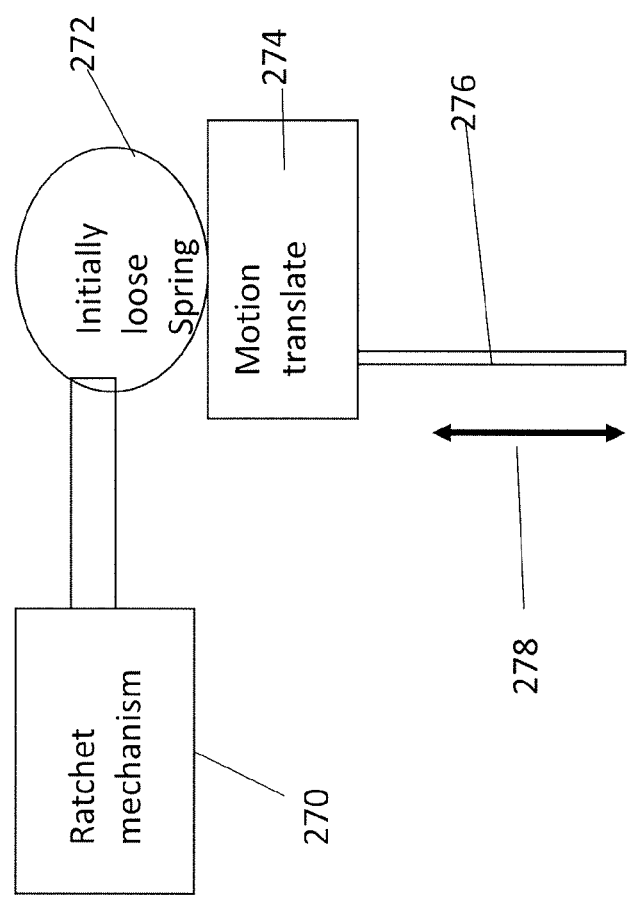
FIG. 19 is a simplified diagram illustrating an external winding mechanism for winding the initially loose spring prior to use, according to an embodiment of the present invention.

Reference is now made to FIG. 19 which illustrates a further embodiment of the present invention in which a ratchet mechanism is provided to wind the spring for the motion translation mechanism. In FIG. 19 there is illustrated a ratchet mechanism 270 which winds or tensions spring 272 which is initially provided loose. As before the unwinding of the spring 272 operates the motion translation mechanism 274 which moves needle 276 to extend and subsequently retract as indicated by arrow 278. The idea is that the spring is installed slack and an external winding system is included for winding the spring after assembly of the injector. That is to say, the embodiment includes an external winding mechanism for the spring 272 powering the needle insertion/retraction. One reason for using such a mechanism is that assembling and/or storing the injector system with an already wound up spring entails various mechanisms of wear and/or failure and/or damage to sensitive and/or expensive components.

Thus the present embodiments permits assembly of the injector while the spring is slack and allows it to be wound up later on and closer to the time of use, typically just before packaging or immediately before providing to the patient.

In use, the spring may be wound in advance or wound up via ratchet 270 after everything is ready. The ratchet is a specific case of the more generic winding mechanism, and only allows the spring to be tensioned and not released.

Figure 20:
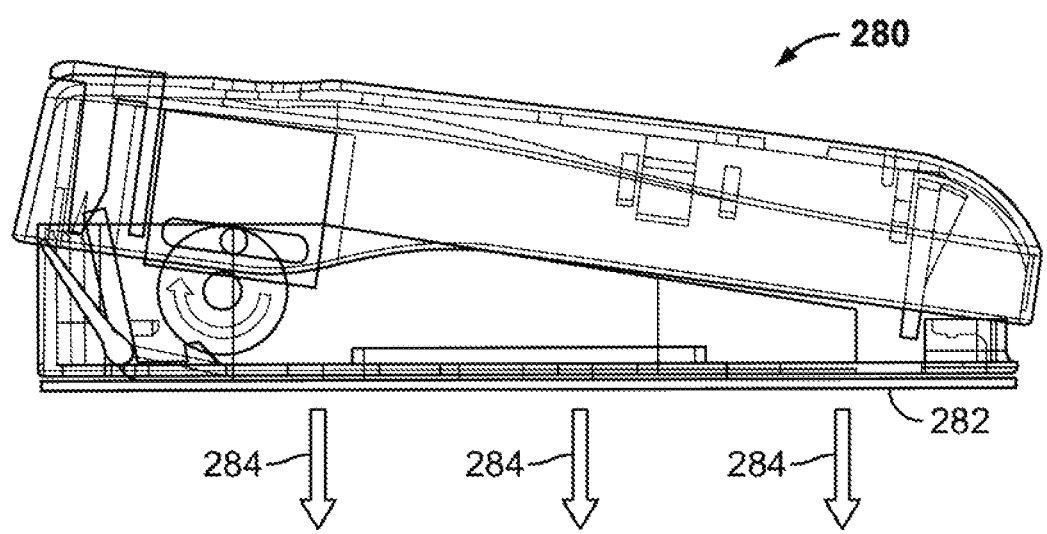
FIG. 20 illustrates an embodiment of the present invention in which adhesion to the skin using an adhesive layer is used to detect the skin and operate the needle retraction mechanism when the injector is withdrawn from the skin.

Reference is now made to FIG. 20, which is a simplified diagram illustrating a further embodiment of the present invention in which injector 280, having adhesive layer 282, uses the adhesive layer to operate retraction of the needle. The adhesive layer 282 acts as the skin sensor in place of latch 296 of the previous embodiments. The adhesive layer is used in any event to keep the injector in position for the duration of the injection process, which in some cases can be an extended duration of time. When the injection is over the injector is removed from the skin but the adhesive has the effect of pulling the base of the injector in the direction of the receding skin and arrows 284. The pull of the skin pushes down the base of the injector and operates the retraction mechanism. Thus, skin detection is provided by the injector base which is adhered to the skin for the injection process. As the base is removed from the skin, the motion pulls the housing and causes retraction of the needle. More particularly, adhesive layer 282 below the base adheres the drug delivery device to the skin of the user for the duration of the injection. Removal of the adhered drug delivery device from the skin and against the adhesion causes a pulling force on the base. The pulling force operates any suitable mechanism to release the interrupter and thereby cause the second motion part which retracts the needle.

Figure 21:
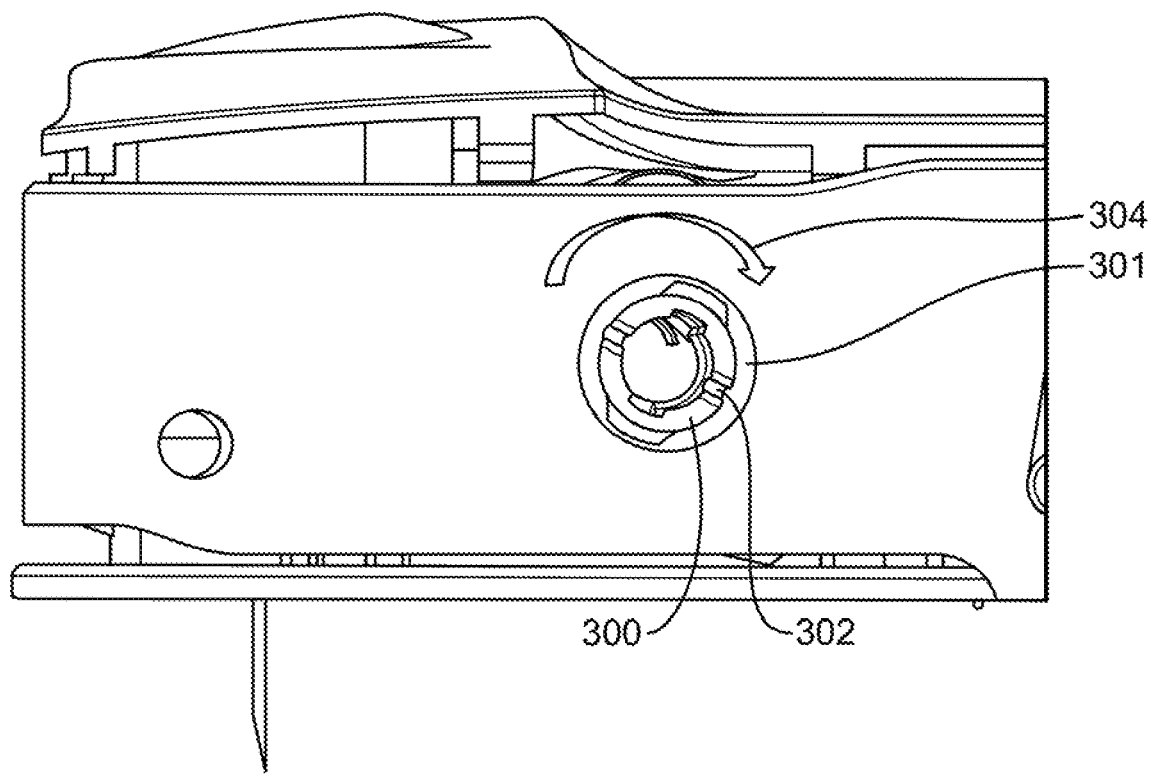
FIG. 21 illustrates an external winding mechanism for winding the coiled spring motion source according to an embodiment of the present invention.

Reference is now made to FIG. 21, which is a simplified diagram illustrating an embodiment allowing the device to be provided with the spring in an unwound state and subsequently wound for use. Assembly and transport of an injector with stored energy can lead to accidental discharge. For example such a discharge may disable the injector and/or destroy valuable medicine. Handling devices with stored energy may be more expensive then handling disarmed devices. In injectors according to the embodiments described above, drive systems may have been inserted into a device fully armed, for example with a spring in compressed state.

The embodiment of FIG. 21 uses a winding mechanism for winding the spring subsequent to loading of the injector. Such a spring can be conveniently wound from outside the device after assembly via an engageable keyhole 300. The keyhole includes a rotating ring 301 which is attached to the spring to be wound and occlusions 302 to engage a correspondingly shaped key so as to turn the ring in the direction of arrow 304 and thus wind the spring.

Figure 22:
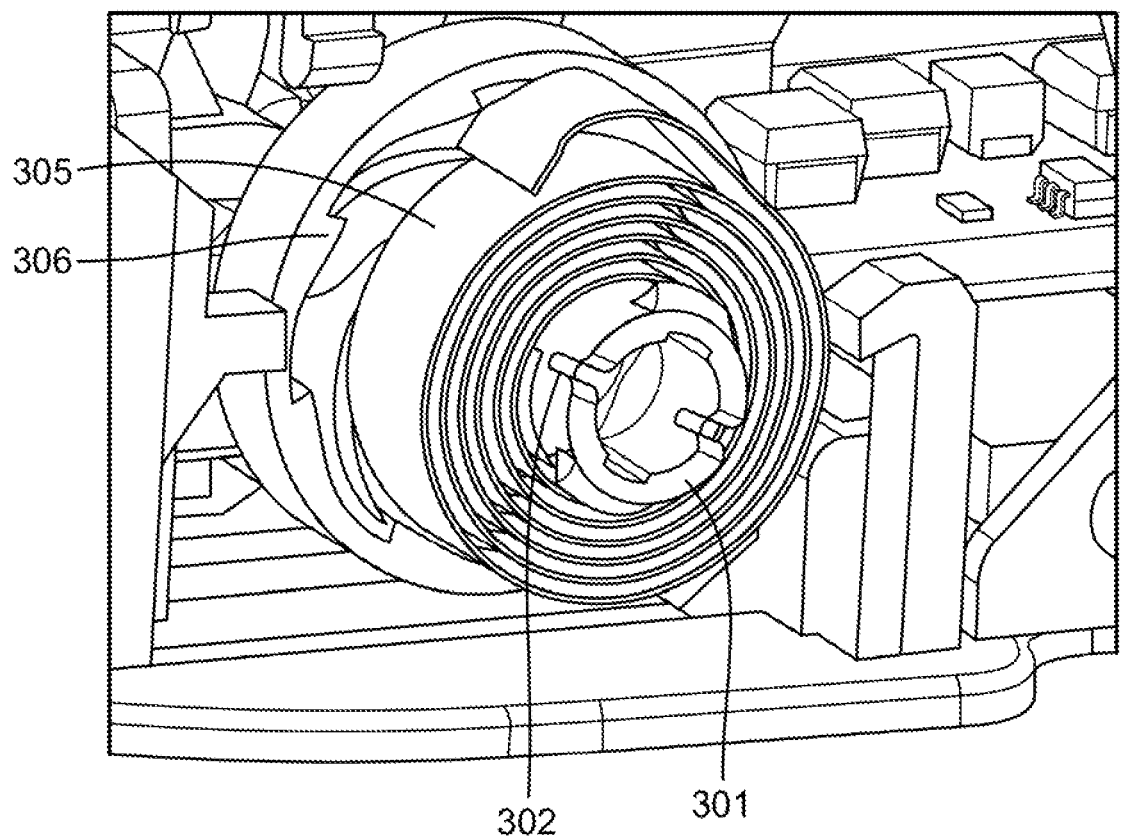
FIG. 22 is a cutaway view showing how the external winding mechanism is connected to the coiled spring.

FIG. 22 shows a cutaway view showing how the ring 301 is connected to the coiled spring 305. Ratchet 306 ensures that the spring is wound in the correct direction.

Rather than assemble the device with the spring already wound the spring is installed slack and an external winding system is included for winding the spring after assembly of the injector. That is to say, the embodiment includes an external winding mechanism for the spring powering the needle insertion/retraction. One reason for using such a mechanism is that assembling and/or storing the injector system with an already wound up spring causes various wear and tear mechanisms which may lead to failure and/or damage to sensitive and/or expensive components.

Thus the present embodiments permit assembly of the injector while the spring is slack and allows the injector to be wound up later on and closer to the time of use, typically just before packaging or immediately before providing to the patient.

When the device is place on the skin, the skin sensor is used for two things.

One purpose is to unlock the button. The skin sensor unlocks the button to allow extension of the needle as discussed hereinabove. In one of the embodiments discussed herein, the skin sensor is pushed down by the skin, and there may be a threshold angle X so that when the sensor reaches an angle Z smaller than the angle X the button is unlocked.

Upon passing the threshold the skin sensor causes unlocking of the trajectory of the coil spring wheel so that the wheel may stop after a half rotation. At the half way position the needle is extended and the mechanism now locks in the extended position to carry out the injection. Later on, as the device is withdrawn, the angle grows and passes the threshold and the mechanism is released a second time for the retraction operation.

In embodiments the design may require that X<Y, for the reason that, if there were not a threshold different from the resting angle, someone with curved or soft skin may put the device on the skin with the sensor at an angle Z wherein X>Z>Y. He would then push the button and the spring would may a full 360 degree turn retracting the needle before it ever injects.

It is noted that in conventional devices, the drive mechanism returns toward its initial state when the needle is retracted. In the present embodiments by contrast the drive continues to further in the same direction while the needle retracts, coming to rest at the opposite end of the rotation from the initial position.

It is expected that during the life of a patent maturing from this application many relevant drug delivery devices and injection mechanisms will be developed and the scopes of the corresponding terms are intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A needle insertion and retraction mechanism for a drug delivery device having a base to be adhered to a surface, comprising:
    a source of continuous motion including a tensioned rotator rotatable about an axis thereof, the rotator being tensioned by a tensioned element connected with the rotator and the tensioned element being configured to unwind said rotator about the axis thereof;
    a user-operated control for said motion source, said control comprising a button and a lever extending at a predetermined angle below the base of the drug delivery device to prevent motion of the button and displaceable from said predetermined angle by the surface, thereby releasing said button;
    an interrupter to stop rotation of said-tensioned rotator at a predetermined location, thereby dividing said rotation into a first motion part and a second motion part, said second motion part being in angular continuity with said first motion part;
    a motion translation mechanism comprising a cam connecting said tensioned rotator to an injection needle, wherein:
    when the lever is displaced from said predetermined angle by the surface and the button is depressed said motion translation mechanism translates rotation of the tensioned rotator into an insertion motion of the injection needle to extend said injection needle during said first motion part, and said interrupter stops the rotation of the rotator at the predetermined location and
    when the lever is thereafter removed from the surface, the interrupter is released and the rotation of the rotator is continued, permitting said motion translation mechanism to translate the continued rotation of the tensioned rotator into a retraction motion of the injection needle to retract said injection needle during said second motion part.

2. The needle insertion and retraction mechanism of claim 1, wherein said tensioned rotator comprises a wheel.

3. The needle insertion and retraction mechanism of claim 2, wherein said tensioned rotator comprises a coiled spring, said coiled spring being connected to unwind said wheel about an axis thereof.

4. The needle insertion and retraction mechanism of claim 1, wherein said lever defines a proximity detector configured to detect surface proximity and to release said interrupter to cause said second motion part on detecting of removal of said device from said surface.

5. The needle insertion and retraction mechanism of claim 1, wherein the lever includes an arm to prevent motion of the button when the lever is extending at said predetermined angle below the base of the drug delivery device, and when said lever is displaced from said predetermined angle by the surface, said arm is moved to release said button.

6. The needle insertion and retraction mechanism of claim 1, further comprising an adhesive layer below said base to adhere said drug delivery device to the surface, removal of said drug delivery device from said surface and against said adhering causing a pulling force on said base, said pulling force causing release of said interrupter to cause said second motion part.

7. The needle insertion and retraction mechanism of claim 1, further comprising a drug level detector configured to detect a level of a drug being administered by said device and to release said interrupter to cause said second motion part on detecting completion of administering said drug.

8. The needle insertion and retraction mechanism of claim 7, wherein said drug level detector comprises a position detector for detecting a position of a plunger pushing said drug being administered into said needle.

9. The needle insertion and retraction mechanism of claim 1, wherein said first and second motion parts are due to successive releases of a single tension source.

10. The needle insertion and retraction mechanism of claim 1, further comprising a tensioning mechanism for allowing external tensioning of said tensioned element.

11. The needle insertion and retraction mechanism of claim 10, wherein said tensioned element is a coiled spring and said tensioning mechanism is a winding mechanism.

12. The needle insertion and retraction mechanism of claim 1, further comprising a latching mechanism for preventing extension of said needle after the needle has been retracted.

13. The needle insertion and retraction mechanism of claim 1, wherein said source of continuous motion is connected to an external winding mechanism for priming prior to use.

14. A method of operating a needle insertion and retraction mechanism comprising:
   adhering a base of a drug delivery device having the needle insertion and retraction mechanism to a surface, wherein the needle insertion and retraction mechanism comprises:
      a source of continuous motion including a tensioned rotator rotatable about an axis thereof, the rotator being tensioned by a tensioned element connected with the rotator, and the tensioned element being configured to unwind said rotator about the axis thereof;
      a user-operated control for said source of continuous motion, said control comprising a button and a lever extending at a predetermined angle below the base of the drug delivery device to prevent motion of the button and displaceable from said predetermined angle by the surface, thereby releasing said button;
      an interrupter to stop rotation of said tensioned rotator at a predetermined location, thereby dividing said rotation into a first motion part and a second motion part, said second motion part being in angular continuity with said first motion part;
      a motion translation mechanism comprising a cam connecting said tensioned rotator to an injection needle
   actuating the button, and, in turn, releasing the tensioned rotator to rotatingly unwind to carry out the first motion part;
   translating said rotation of the rotator into an insertion motion of an injection needle to extend said injection needle during said first motion part, said interrupter stopping the rotation of the rotator at the predetermined location;
   releasing said drug delivery device from the surface, thereby releasing the interrupter from the rotator such that rotation of the rotator is continued to carry out said second motion part, said second motion part being directionwise continuous with said first motion part; and
   translating said rotation of the rotator during said second motion part into a retraction motion of said injection needle.

15. The method of claim 14, wherein said first and second motion parts are due to successive releases of a single tension source.

* * * * *